(12) United States Patent
Thurin et al.

(10) Patent No.: US 11,896,311 B2
(45) Date of Patent: Feb. 13, 2024

(54) OPHTHALMIC IMAGING SYSTEM

(71) Applicant: King's College London, London (GB)

(72) Inventors: Brice Thurin, London (GB); Christos Bergeles, London (GB)

(73) Assignee: King's College London, London (GB)

( * ) Notice: Subject to any disclaimer, the term of this patent is extended or adjusted under 35 U.S.C. 154(b) by 822 days.

(21) Appl. No.: 16/929,521

(22) Filed: Jul. 15, 2020

(65) Prior Publication Data

US 2020/0345230 A1 Nov. 5, 2020

Related U.S. Application Data

(63) Continuation of application No. PCT/GB2019/050099, filed on Jan. 15, 2019.

(30) Foreign Application Priority Data

Jan. 15, 2018 (GB) ..................................... 1800623

(51) Int. Cl.
*A61B 3/14* (2006.01)
*A61B 3/12* (2006.01)

(52) U.S. Cl.
CPC ............... *A61B 3/145* (2013.01); *A61B 3/12* (2013.01)

(58) Field of Classification Search
CPC .. A61B 3/145; A61B 3/12; A61B 3/13; A61B 3/14; H04N 23/55; G02B 27/0075
USPC ........................................................ 351/206
See application file for complete search history.

(56) References Cited

U.S. PATENT DOCUMENTS

| 7,290,880 | B1 | 11/2007 | Yaron et al. |
| 8,488,895 | B2* | 7/2013 | Muller ............... G02B 21/0048 382/128 |
| 8,998,411 | B2 | 4/2015 | Tumlinson et al. |
| 9,295,388 | B2 | 3/2016 | Lawson et al. |
| 2010/0128221 | A1* | 5/2010 | Muller .................. A61B 3/1025 348/78 |
| 2012/0162212 | A1* | 6/2012 | Takahashi ............ H04N 13/315 345/419 |
| 2013/0010260 | A1* | 1/2013 | Tumlinson ............. A61B 3/152 351/246 |
| 2013/0063699 | A1 | 3/2013 | Goldfain et al. |

(Continued)

FOREIGN PATENT DOCUMENTS

| EP | 2769666 | 8/2014 |
| EP | 3020326 | 5/2016 |

(Continued)

OTHER PUBLICATIONS

"Ophthalmic instruments—Fundus cameras" ISO standard ISO10940:2009.

(Continued)

*Primary Examiner* — Mohammed A Hasan
(74) *Attorney, Agent, or Firm* — Levine Bagade Han LLP

(57) ABSTRACT

An ophthalmic imaging system comprises a first imaging subsystem, a sensor array and a second imaging subsystem. The first imaging subsystem forms a primary image of the interior of an eye through the diameter of the eye pupil. The second imaging subsystem comprises a lens array to form an array of secondary images on the sensor array. The lens array is composed of a plurality of types of lenses, each type having a different optical power.

16 Claims, 12 Drawing Sheets

(56) References Cited

U.S. PATENT DOCUMENTS

2016/0278637 A1 9/2016 Gao et al.
2018/0063502 A1* 3/2018 Ogawa .................. H04N 13/31

FOREIGN PATENT DOCUMENTS

| WO | WO 2017/063715 | 4/2017 |
|----|----|----|
| WO | WO 2019/138254 | 7/2019 |

OTHER PUBLICATIONS

Boominathan, Vivek et al., "Improving Resolution and Depth-of-Field of Light Field Cameras Using a Hybrid Imaging System", 2014 IEEE International conference on computational photography, May 2014.

Dannberg, Peter et al., "Wafer-Level Hybrid Integration of Complex Micro-Optical Modules", Micromachines, 5, No. 2, pp. 325-340, Jun. 5, 2014.

Georgiev, Todor et al., "The Multi-Focus Plenoptic Camera", in Digital Photography VIII, XP055583884, Retrieved from the Internet: URL:https://pdfs.semanticscholar.org/6fd8/d4081eabf4bd3475c0b32cc2aa21aa51ae76.pdf [retrieved on Apr. 26, 2019], Jan. 24, 2012.

Li, Tian-Jiao et al., "Multi-focused microlens array optimization and light field imaging study based on Monte Carlo method", Optics Express, vol. 25, No. 7, pp. 8274-8287, Apr. 3, 2017.

Lumsdaine, Andrew et al., "The Focused Plenoptic Camera", In Computational Photography (ICCP), 2009.

Ng, Ren, "Digital light field photography", Doctoral Thesis, 2006.

Perwass, Christian et al., "Single Lens 3D-Camera with Extended Depth-of-Field", Raytrix GmbH, Schauenburgerstr. 116, 24116 Kiel, Germany, InSPIE Elect. Imaging, 2012.

Wang, Yuwang et al., "The Light Field Attachment: Turning a DSLR into a Light Field Camera Using a Low Budget Camera Ring", IEEE Transactions on Visualization and Computer Graphics, vol. 23, No. 10, pp. 2357-2364, Oct. 2017.

* cited by examiner

OPHTHALMIC IMAGING SYSTEM

CROSS-REFERENCE TO RELATED APPLICATIONS

This application is a continuation International Patent Application Number PCT/GB2019/050099 filed Jan. 15, 2019, which claims the benefit of priority to GB 1800623.9 filed Jan. 15, 2018, the contents of which are incorporated herein by reference in their entireties.

BACKGROUND OF THE INVENTION

1. Field of the Invention

This invention relates generally to imaging of the eye, for example during eye examination or during eye surgery. More particularly the present invention relates to an ophthalmic imaging system, a vitreoretinal surgical imaging system, a method of performing ophthalmic imaging, a method of diagnosing a medical condition and a method of manufacturing an ophthalmic imaging system.

2. Description of the Related Art

Retina fundus imaging is a critical task in routine eye examination and surgical procedure. It is typically performed by a fundus camera. The requirements for the optical properties of a Fundus camera are provided in ISO standard ISO10940:2009 ("Ophthalmic instruments—Fundus cameras"). The resolving power of the fundus camera optics on the fundus is the minimum separation allowing recognition of two adjacent lines on the fundus. It is expressed as number of lines pairs per millimeter (lp/mm). For a fundus camera with a field of view larger than 30 degrees, the requirements are a minimum of 60 lp/mm in the center of the field of view and a minimum of 25 lp/mm at the periphery.

Vitreoretinal surgery, i.e. the manipulation of sub-millimeter structures on the retinal surface, takes place under high-magnification stereo microscopy. It limits the maximally attainable depth-of-field and requires constant manual adjustment of microscope focus with every eye motion. Additionally, high magnification combined with stereo viewing hinders depth perception, forcing surgeons to rely on complementary cues, such as shadows, to understand the proximity of their tools to the sensitive retina.

A light-field sensor is a photodetectors array with a lenslets array in front it. A first type of light-field sensor arrangement is described by R. Ng in his doctoral thesis ("Digital light field photography", 2006). In this arrangement, an objective lens form an image of a scene on the lenslets array. The light passing through the lenslets array is collected with the photodetectors array. The resolution of the image is equal to the number of lenslets. The photodetectors array records the direction of the light rays hitting the lenslets array.

A second light-field sensor arrangement has been described by A. Lumsdaine and T. Georgiev ("The Focused Plenoptic Camera". In Computational Photography (ICCP), 2009). In this arrangement, an objective lens forms a primary image of a scene. Each element of a lenslets array reimages part of the primary image onto the photodetectors array, creating an array of sub-images. This arrangement is analogue to a packed array of micro-cameras, each of which captures unique but overlapping micro-images.

By sampling both the spatial and angular domains, the user is given the tools to manipulate focus, perspective, and depth of field (DOF) during post-processing. With traditional imaging, these attributes are largely fixed once the image is acquired.

U.S. Pat. No. 8,998,411B2 discloses systems and methods for applying the concept of light-field sensors to fundus photography. A primary optical system serves to transport light from the object towards the light-field sensor. The magnification of the primary optical system is set such that the field of view of the system matches the size of the sensor. Further an aperture stop is added between an objective lens and a reimaging lens to prevent overlap between adjacent lenslets' images on the sensor array. A reimaging lens is placed between the aperture stop and the light-field sensor. The reimaging lens forms an image of the retina on top of the lenslets array.

WO2017/063715A1 describes a system and method for which a light-field camera is used to capture a digital image of the surgical field including the eye.

EP2769666 discloses an integral imaging system for capturing an integral photograph of the fundus. This integral photograph enables projecting a three-dimensional image and generating topographical maps of the fundus. The lenslets array is arranged, in conjunction with the external optic system of the eye of the patient and the ophthalmoscopic lens, to form an image of the pupil of the eye on the array sensor.

EP3020326A2 discloses a multimode fundus camera capturing filtered and three-dimensional images of the eye. In one embodiment, the system is equipped with a light-field sensor wherein the lenslets array is located on the imaging plane of the main lens and an image of the pupil of the eye is formed on top of the sensor array.

U.S. Pat. No. 9,295,388B2 discloses retinal imaging devices that may be head-worn and may allow a user to self-image her or his retina. In an exemplary embodiment, the imaging sensor is replaced by a light-field sensor.

The present invention discloses a high resolution retinal imaging system embedding a light-field sensor. It is well known to those skilled in the art that light-field cameras suffer from poor imaging resolution. This limitation is not addressed in the prior art.

The resolution requirements imposed by the ISO standard 10940:2009 are challenging to achieve for a light-field sensor. Not any light-field sensor can be used for this application. Current and commercially available sensors do not meet the specifications to fulfil these requirements. It may not be sufficient to have a primary optical system matching the form factor and sensor size of the light-field sensor. It is preferable for the light-field sensor specifications to match the eye optical properties to obtain the required resolution.

It is desirable to provide an ophthalmic imaging system that has the advantages of a light-field sensor, and has improved imaging resolution compared to the prior art.

An aim of this invention is to provide a retinal imaging system that can be implemented into an ophthalmic diagnostic instrument fulfilling the international standard requirements.

Another aim of this invention is to provide a retinal imaging system that can be implemented into an ophthalmic surgical microscope. The instrument is to improve depth perception and eliminate the need to manually refocus during surgery and to provide guidance to the surgeon or surgical robots.

SUMMARY OF THE INVENTION

The present invention attempts to address these aims by providing an ophthalmic imaging system, a vitreoretinal surgical imaging system, a method of performing ophthalmic imaging, a method of diagnosing a medical condition, and a method of manufacturing an ophthalmic imaging system.

An ophthalmic imaging system preferably comprises a first imaging subsystem configured to form a primary image of the interior of an eye through the diameter of the eye pupil. The ophthalmic imaging system preferably comprises a sensor array. The ophthalmic imaging system preferably comprises a second imaging subsystem comprising a lens array configured to form an array of secondary images on the sensor array. Preferably, the lens array is composed of a plurality of types of lenses, each type having a different optical power.

An ophthalmic imaging system preferably comprises a first imaging subsystem configured to form a primary image of the interior of an eye through the diameter of the eye pupil. The ophthalmic imaging system preferably comprises a sensor array. The ophthalmic imaging system preferably comprises a second imaging subsystem comprising a lens array configured to form an array of secondary images on the sensor array. Preferably, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centered on the centers of the lenses (R) obey the relation $$\frac{b}{d} = \frac{Xe}{D}\left(\frac{1}{\frac{D}{4R}-1}\right), \text{ where } X \leq 82.$$

Optionally, the system is diffraction limited continuously over a depth range of planes to be imaged, wherein for part of the range a first type of lens having a first optical power is diffraction limited and for another part of the range a second type of lens having a second optical power is diffraction limited.

Optionally, for each type of lens of the lens array, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centered on the centers of the lenses (R) obey the relation $$\frac{b}{d} = \frac{Xe}{D}\left(\frac{1}{\frac{D}{4R}-1}\right), \text{ where } X \leq 82.$$

Optionally, X≤24. Optionally, X≤5.0. Optionally, X≥0.50. Optionally, the lens array is arranged such that X is variable. Optionally, the lens array comprises a spatial modulator or micro optics with controllable moving parts Optionally, D=7 mm and e=17 mm.

Optionally, for each type of lens of the lens array, the optical distance between the lenses and the sensor array (b) and the diameter of the lenses (d) obey the relation $$\frac{b}{d} \leq 6.8.$$

Optionally, for each type of lens of the lens array, the optical distance between the lenses and the sensor array (b) and the diameter of the lenses (d) obey the relation $$\frac{b}{d} \geq 2.9.$$

Optionally, the first imaging subsystem comprises an objective lens group, a first intermediate lens group and a second intermediate lens group, wherein in use the first intermediate lens group and the second intermediate lens group are configured to be positioned optically between the objective lens group and the eye pupil.

Optionally, the first intermediate lens group and the second intermediate lens group are configured to relay an image of the eye pupil onto the principal plane of the objective lens group.

Optionally, the first intermediate lens group and the second intermediate lens group are configured to magnify the image of the eye pupil by a ratio f141/f142 where f141 is the focal length of the first intermediate lens group and f142 is the focal length of the second intermediate lens group. Optionally, for each type of lens of the lens array, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centered on the centers of the lenses (R) obey the relation $$\frac{b}{d} = \frac{Xe}{D}\left(\frac{1}{\frac{D}{4R}-\frac{f142}{f141}}\right), \text{ where } X \leq 82.$$

Optionally, the first imaging subsystem comprises an objective lens group configured to be positioned such that the eye pupil or an image of the eye pupil is at the back focal plane of the objective lens group. Optionally, for each type of lens of the lens array, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centered on the centers of the lenses (R) obey the relation $$\frac{b}{d} = \frac{4XRe}{D^2}, \text{ where } X \leq 82.$$

Optionally, the first imaging subsystem is a variable power imaging subsystem.

Optionally, the lens array is composed of three types of lenses, each type having a different optical power. Optionally, the lens array is composed of four types of lenses, each type having a different optical power. Optionally, the lens array is composed of five types of lenses, each type having a different optical power. Optionally, the lens array is composed of six types of lenses, each type having a different optical power. Optionally, the lens array is composed of seven types of lenses, each type having a different optical power.

Optionally, for each type of lens of the lens array, the lenses are regularly distributed across the lens array. Optionally, the lenses of the lens array are regularly tessellated or semiregularly tessellated. Optionally, the lenses of the lens array are irregularly tessellated.

Optionally, the primary image is formed in front of the lens array. Optionally, the primary image is formed behind the lens array.

Optionally, the optical power of the lenses of the lens array is positive. Optionally, the optical power of the lenses of the lens array is negative. Optionally, the optical power of a first type of lens is of different sign from the optical power of a second type of lens. Optionally, lenses of different type have different circumradius. Optionally, the distance between the lenses and the sensor array is different from one lens to another within the lens array. Optionally, the distance between the lenses and the sensor array is different from one type of lens to another. Optionally, the lens array comprises achromatic lenses. Optionally, the lens array comprises aspherical lenses. Optionally, the lens array comprises a diffractive lens.

Optionally, the lens array comprises rod lenses.

Optionally, the system comprises two or more lens arrays configured to form the secondary images on the sensor array.

A vitreoretinal surgical imaging system preferably comprises the system.

A method of performing ophthalmic imaging preferably comprises using a first imaging subsystem to form a primary image of the interior of an eye through the diameter of the eye pupil. The method preferably comprises using a second imaging subsystem comprising a lens array to form an array of secondary images on a sensor array. The lens array is preferably composed of a plurality of types of lenses, each type having a different optical power.

A method of performing ophthalmic imaging preferably comprises using a first imaging subsystem to form a primary image of the interior of an eye through the diameter of the eye pupil. The method preferably comprises using a second imaging subsystem comprising a lens array to form an array of secondary images on a sensor array. Preferably, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centered on the centers of the lenses (R) obey the relation $$\frac{b}{d} = \frac{Xe}{D}\left(\frac{1}{\frac{D}{4R} - 1}\right), \text{ where } X \leq 82.$$

A method of diagnosing a medical condition preferably comprises the method.

A method of manufacturing an ophthalmic imaging system preferably comprises providing a first imaging subsystem configured to form a primary image of the interior of an eye through the diameter of the eye pupil. The method preferably comprises providing a sensor array. The method preferably comprises providing a second imaging subsystem comprising a lens array configured to form an array of secondary images on the sensor array. The lens array is preferably composed of a plurality of types of lenses, each type having a different optical power.

A method of manufacturing an ophthalmic imaging system preferably comprises providing a first imaging subsystem configured to form a primary image of the interior of an eye through the diameter of the eye pupil. The method preferably comprises providing a sensor array. The method preferably comprises providing a second imaging subsystem comprising a lens array configured to form an array of secondary images on the sensor array. Preferably, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centered on the centers of the lenses (R) obey the relation $$\frac{b}{d} = \frac{Xe}{D}\left(\frac{1}{\frac{D}{4R} - 1}\right), \text{ where } X \leq 82.$$

Optionally, the first imaging subsystem comprises an objective lens group configured to be positioned such that the eye pupil or an image of the eye pupil is at the back focal plane of the objective lens group.

Optionally, for each type of lens of the lens array, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centered on the centers of the lenses (R) obey the relation $$\frac{b}{d} = \frac{4XRe}{D^2}, \text{ where } X \leq 82.$$

BRIEF DESCRIPTION OF THE DRAWINGS

The present invention will now be described, by way of non-limitative example only, with reference to the accompanying drawings, in which.

DETAILED DESCRIPTION

Figure 1:
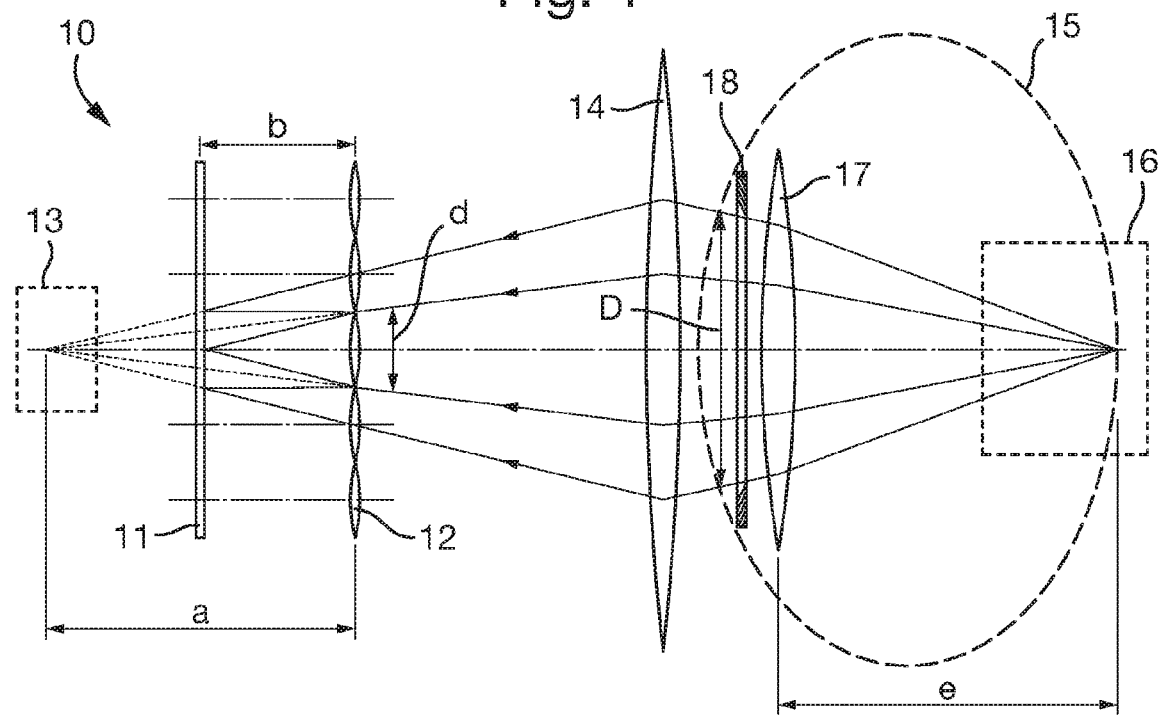
FIGS. 1 to 3 are schematic diagrams illustrating optical layouts according to the invention.

The present invention includes a custom focused lightfield sensor; the said sensor principle was described by T. Georgiev and A. Lumsdaine ("The multifocus plenoptic camera", in Digital Photography VIII, 2012). One of the advantages of the present invention is the ability to reconstruct high-resolution images of planes located at different depth inside the eye, e.g. planes located several millimeters away from the retina can be reconstructed.

The micro-images recorded by the light-field sensor contain overlapping area of retinal planes seen along a different line of sight. The amount of parallax between two micro-images is set by the limiting optical aperture. To maximize the parallax the limiting optical aperture of the imaging system must be the eye pupil. In the present invention, preferably no aperture stop is added to prevent cross-talk between micro-images. Instead an objective lens optionally with variable optical power forms a primary image of the retina.

The high-resolution light-field fundus imager is composed of the custom focused light-field sensor tailored to the anatomical structure of the eye and an optionally variable power objective lens. The objective lens is positioned in front of the eye and forms an image of the interior of the eye (including the retina, vitreous humour and the eye lens). The micro-lenses array forms a multitude of micro-images of the objective lens image on top of the sensor array. The micro-lenses array can be composed of several micro-lenses arrays interlaced. The arrays of micro-lenses can be positioned on a regular or irregular grid. The micro-lenses can have different optical power. The micro-lenses can be positioned at different axial locations from each other. The micro-lenses can have different apertures or diameters. The imaging system is so designed that the lateral imaging resolution provided by the invention is sufficient to image small anatomical structures of the eye.

The ophthalmic imaging system 10 of the invention comprises a first imaging sub system. The first imaging subsystem comprises an objective lens 14. The first imaging subsystem is configured to form a primary image 13 of the interior of an eye 15 through the diameter of the eye pupil 18. The ophthalmic imaging system 10 comprises a sensor array 11. The ophthalmic imaging system 10 comprises a second imaging subsystem. The second imaging subsystem comprises a lens array 12. The lens array 12 is configured to form an array of secondary images on the sensor array 11.

Optionally, the ophthalmic imaging system 10 comprises a light source. The light source is configured to generate light that enters the eye 15 through the eye pupil 18. Optionally, the light source comprises an LED. Optionally, the ophthalmic imaging system 10 comprises a polarizer configured to polarize light emitted by the light source.

The invention is an apparatus capable of imaging a three-dimensional volume 16 of the back of an eye 15 as illustrated. The eye lens 17 and the objective lens 14 form a primary image 13 of volume 16. The lens array 12 projects an array of partial images of volume 16 onto the sensor array 11. Each point within volume 16 is present in a plurality of the partial images. To be able to locate a point within volume 16, each point must be present in at least two partial images. This condition is satisfied if the magnification of the lens array 12 is given by $m \leq 1/v$. The magnification of the lens array 12 is given by the equation $m=a/b$, where the optical distance between the primary image point (i.e. the point shown in FIGS. 1 and 2 where the rays that form the primary image 13 converge) and the lenses of the lens array 12 is a, and the optical distance between the sensor array 11 and the lenses of the lens array 12 is b. The parameter v is a function of the geometrical configuration of the lens array 12. For a one-dimensional array of identical lenses, $v=2$. Hence, for a one-dimensional array of equally sized lenses, parallax can be used if the magnification of the lens array 12 is given by $m \leq 1/2$. The primary image 13 can also be located behind lens array 12 as shown.

Preferably the eye pupil 18 with a diameter D is the limiting optical aperture of the imaging system. This is to ensure the maximum possible parallax between the partial images. The optical distance between the eye lens 17 and a reference plane of the object to be imaged, such as the retina at the back of the eye, is e. The diameter of a single lens of the lens array 12 is d and as mentioned above the distance between the sensor array 11 and the lenses of the lens array 12 is b. By using a light-field sensor, it is possible to refocus at different planes away from the reference plane, e.g. the retina.

When $m=1/v$, parallax can be used when imaging the reference plane. Additionally, parallax can be used when imaging other planes (i.e. refocusing planes) that are in front of the reference plane (i.e. between the retina and the eye lens). However, parallax could not be used when imaging planes behind the reference plane. The condition $m=1/v$ represents the limit for parallax to be used when imaging the reference plane.

Optionally the ophthalmic imaging system 10 satisfies equation 1 below:

$$\frac{b}{d} = \frac{Xe}{D}\left(\frac{1}{\frac{D}{4R}-1}\right),$$

where X is less than or equal to 82. In equation 1, the parameter R depends on the geometry of the lens array 12. The parameter R is related to the earlier-mentioned parameter v by the relation $$v = \frac{d}{4R}.$$

The parameters v and R relate to the minimum requirements for parallax to be used. This is related to the requirement that each image point is imaged in at least two different photo detectors of the sensor array 11 by being focused through at least two different lenses of the lens array 12.

The parameter R is the minimum radius of circle required for the lens array 12 to be covered by circles having the minimum radius if the circles were centered on the centers of the lenses of the lens array 12. Examples of the parameter R, together with the lens diameter d are shown in FIGS. 4-11. The parameter R represents the minimum radius of projection cone to achieve a total covering of the two-dimensional projection plane of the lens array 12.

The diffraction-limited resolution is the theoretical maximum resolution of the ophthalmic imaging system 10. The diffraction-limited resolution can drop off as the refocusing plane moves away from the retina. By providing an upper limit of 82 for X, the diffraction-limited resolution drops off less quickly compared to prior art systems as the refocusing plane moves away from the retina.

A single equivalent thin lens can represent the combined optics of the eye 15 and the first imaging subsystem of the ophthalmic imaging system 10. The optical position of the single equivalent thin lens is similar to the optical position of the eye lens 17. Therefore, in the calculations below, the optical position of the eye lens 17 is used as an approximation for the optical position of the single equivalent thin lens that can represent the combined optics of the eye 15 and the first imaging subsystem of the ophthalmic imaging system 10. The diffraction-limited resolution is related to the projection of the sensor blur spot on the retinal space by equation 2 below:

$$u = \frac{sga}{hb},$$

where s is the diffraction-limited spot size, g is the optical distance between the eye lens 17 and the refocusing plane (i.e. g is smaller than e when refocusing on a plane that is closer to the eye lens 17) and h is the optical distance between the eye lens 17 and the primary image point. This can be rewritten in terms of the focal length f of the lenses of the lens array 12 as shown in equation 3 below:

$$u = \frac{1.22\lambda g}{d}\left(1 + \left(\frac{1}{\frac{1}{b}-\frac{1}{f}} - \frac{Db}{d}\right)\left(\frac{d}{Db} + \frac{1}{e} + \frac{1}{g}\right)\right),$$

where λ is the wavelength of light used. Equation 3 shows how the diffraction-limited resolution varies depending on the position of the refocusing plane (represented by the value g).

The diffraction-limited resolution can be made independent of the position of the refocusing plane (i.e. independent of g) if equation 1 above is satisfied with X=1. According to the invention, X≤82, which is closer to 1 compared to ophthalmic imaging systems known in the prior art. As a result, the diffraction-limited resolution drops off less quickly for refocusing planes moving away from the retina. Preferably equation 1 is satisfied with X≤50, X≤24, X≤20, X≤10, X≤5.0, or X≤2.0.

Preferably, the ophthalmic imaging system 10 is a system where the lateral resolution is identical for any two-dimensional image slices of volume 16 taken at different depths or axial position. This is accomplished for the parameters of the lens array 12 obeying equation 1, with X=1.

Preferably, the ophthalmic imaging system 10 is a high-resolution light-field imaging unit composed of a variable focus objective lens 14 coupled with a lens array 12 and a sensor array 11 obeying equation 1 with X≤82. The variable focus objective lens 14 is configured to adjust the focusing distance of the primary image 13 to match its effective f-number, i.e. the ratio of the image distance to the diameter of the optical aperture, with the effective f-number of the lenses of the lens array 12. The variable focus objective lens 14 is configured to compensate for variation among the population of the diameter of the eye pupil 18.

Optionally the lens array 12 is composed of a plurality of types of lenses, each type having a different optical power. By providing a plurality of types of lenses of different optical powers, the depth-of-field can be increased. Each type of lens has a different focal length. Each type of lens has a resolution peak corresponding to a different distance from the reference plane, e.g. the retina. As a result, the depth-of-field is increased. The image resolution is greater over a depth range of distances from the retina.

Figure 2:
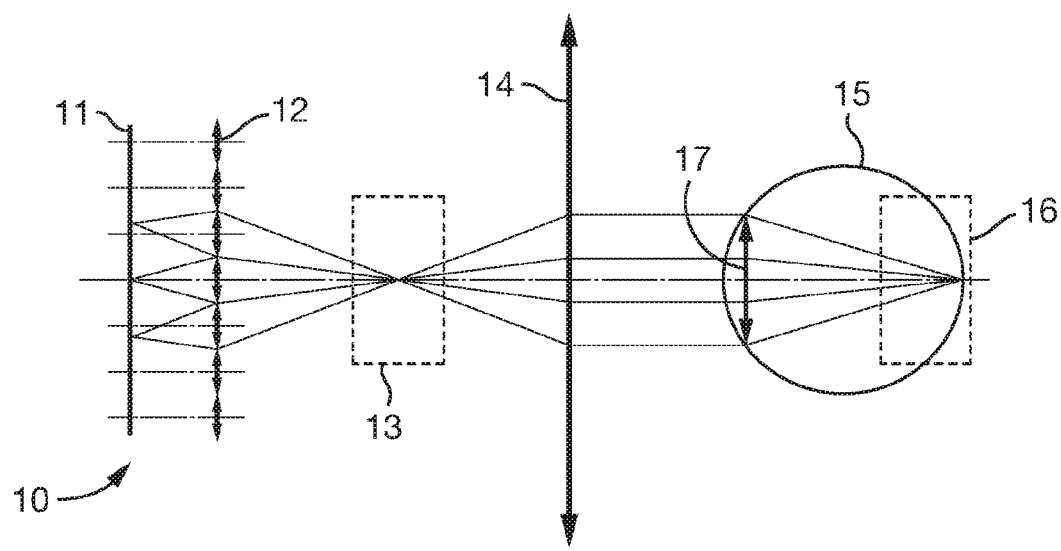
Figure 3:
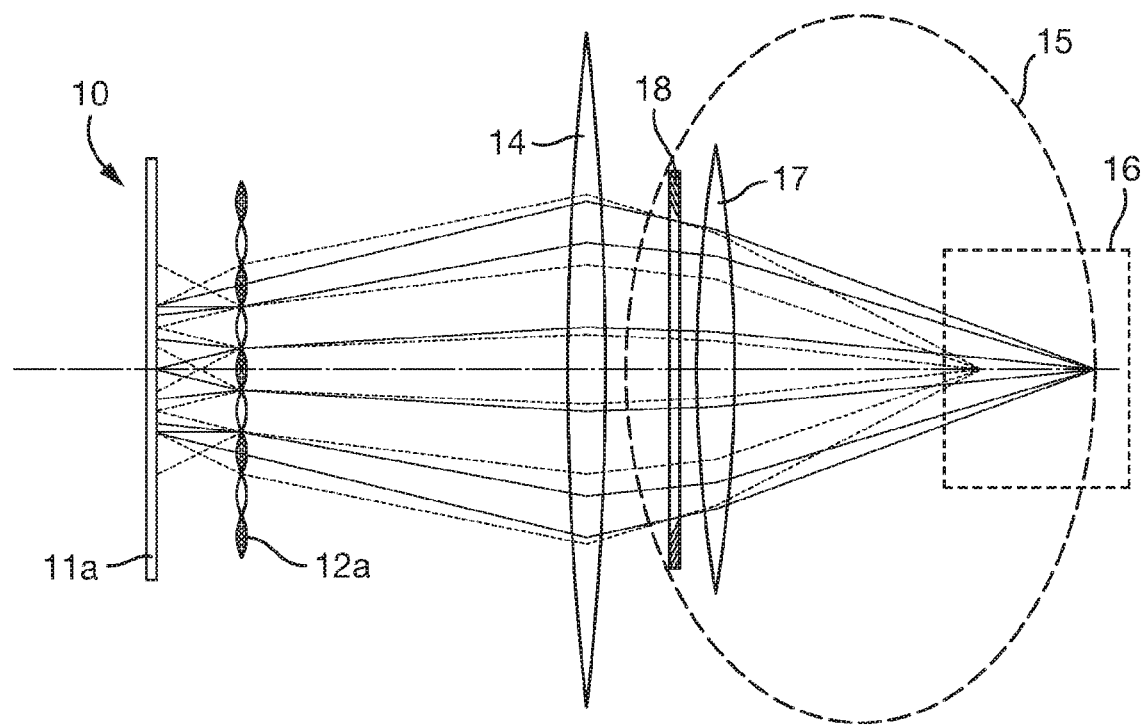
Figure 4:
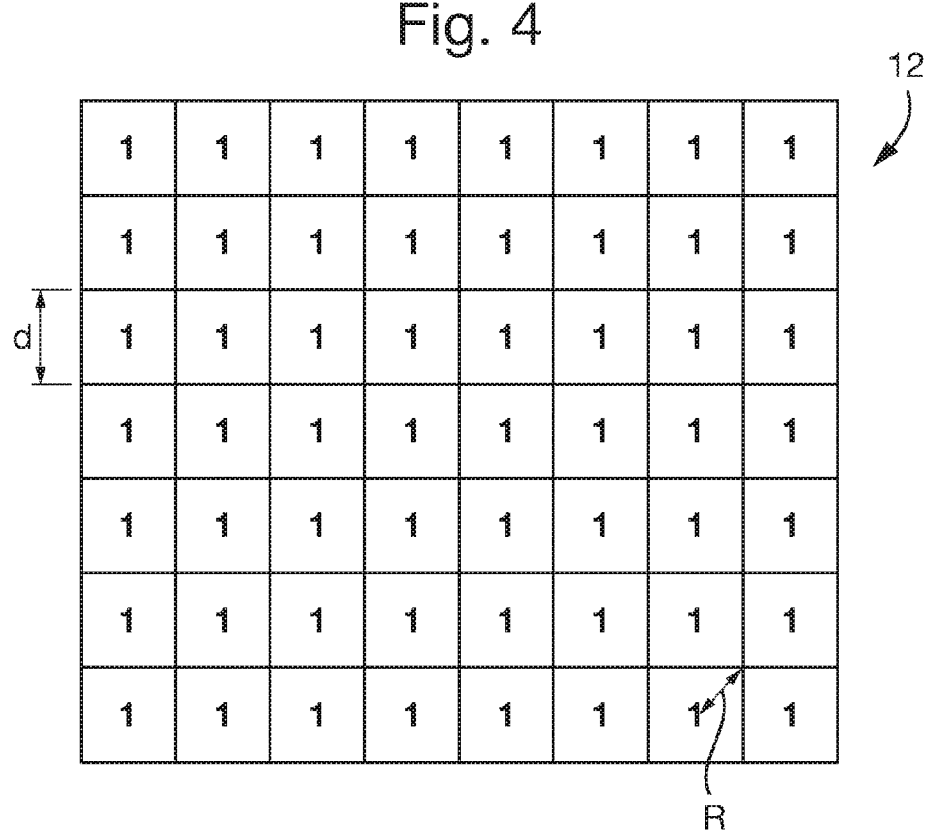
FIGS. 4 to 11 are schematic diagrams of lens arrays according to the invention.
Figure 5:
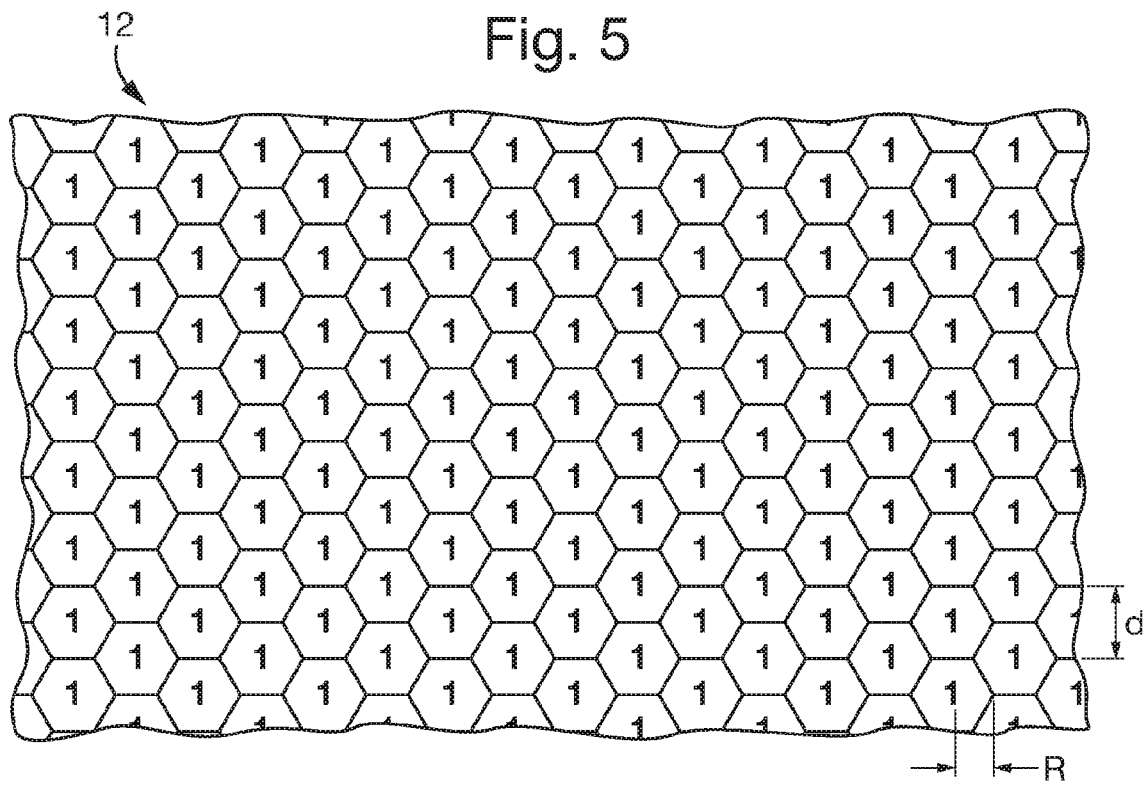

As shown in FIG. 1, optionally the imaging lens group (e.g. the objective lens 14) is in substantially the same plane as the eye lens 17.

Figure 16:
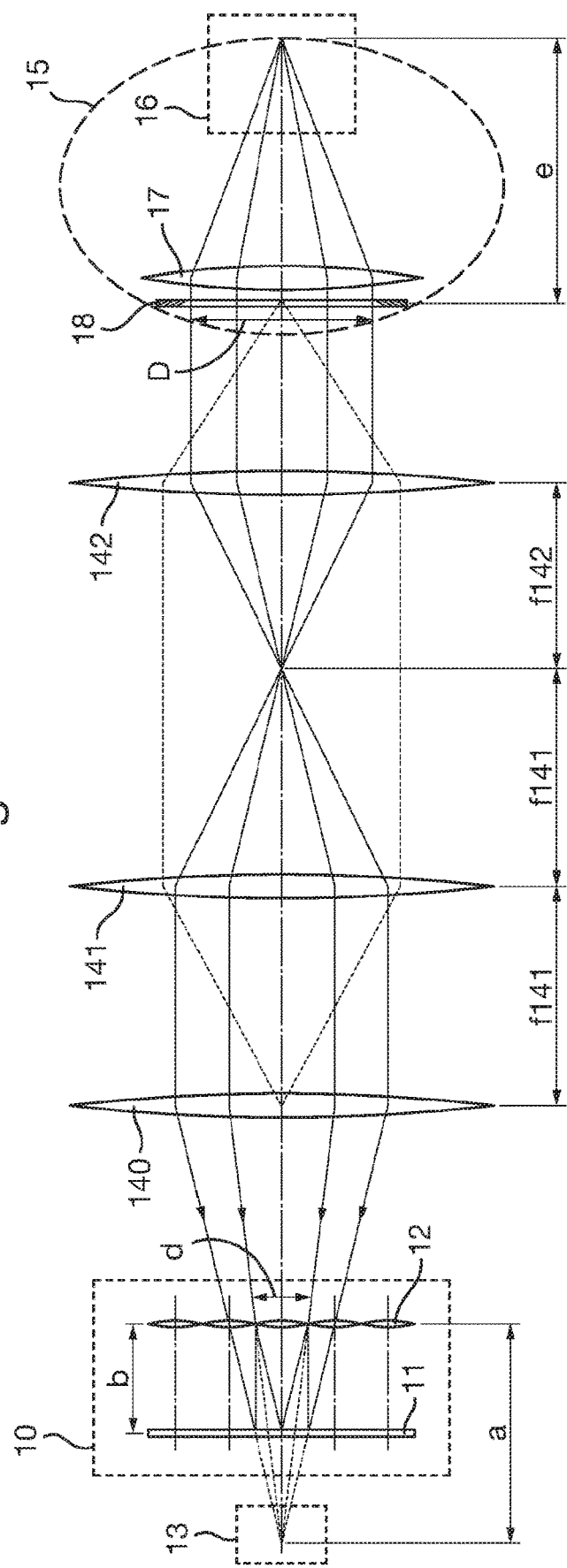
FIGS. 16 to 18 are schematic diagrams illustrating optical layouts according to the invention.

FIG. 16 is a schematic diagram illustrating an optical layout according to the invention. As shown in FIG. 16, optionally the imaging lens group (e.g. the objective lens 14) is at a plane that is conjugate to the plane of the eye lens 17.

As shown in FIG. 16, two or more groups of lenses 141, 142 can be added. Optionally, the first imaging subsystem comprises an objective lens group 140, a first intermediate lens group 141 and a second intermediate lens group 142. The first intermediate lens group 141 and the second intermediate lens group 142 are between the objective lens group 140 and the eye lens 17. The first intermediate lens group 141 and the second intermediate lens group 142 are configured to relay an image of the eye pupil 18 onto the principal plane of the objective lens group 140. These intermediate lens groups 141, 142 have a primary function to relay an image of the eye pupil 18 onto the entrance aperture of the imaging lens group 140.

Optionally, a secondary function of the telescope composed of the intermediate lens groups 141, 142 is to magnify by the ratio f141/f142 the diameter of the eye pupil. The first intermediate lens group 141 and the second intermediate lens group 142 are configured to magnify the image of the eye pupil 18 by a ratio f141/f142 where f141 is the focal length of the first intermediate lens group 141 and f142 is the focal length of the second intermediate lens group 142.

Optionally, for each type of lens of the lens array, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centered on the centers of the lenses (R) obey the relation $$\frac{b}{d} = \frac{Xe}{D}\left(\frac{1}{\frac{D}{4R} - \frac{f142}{f141}}\right), \text{ where } X \leq 82.$$

Preferably, this equation is satisfied with X≤50, X≤24, X≤20, X≤10, X≤5.0, or X≤2.0.

Figure 17:
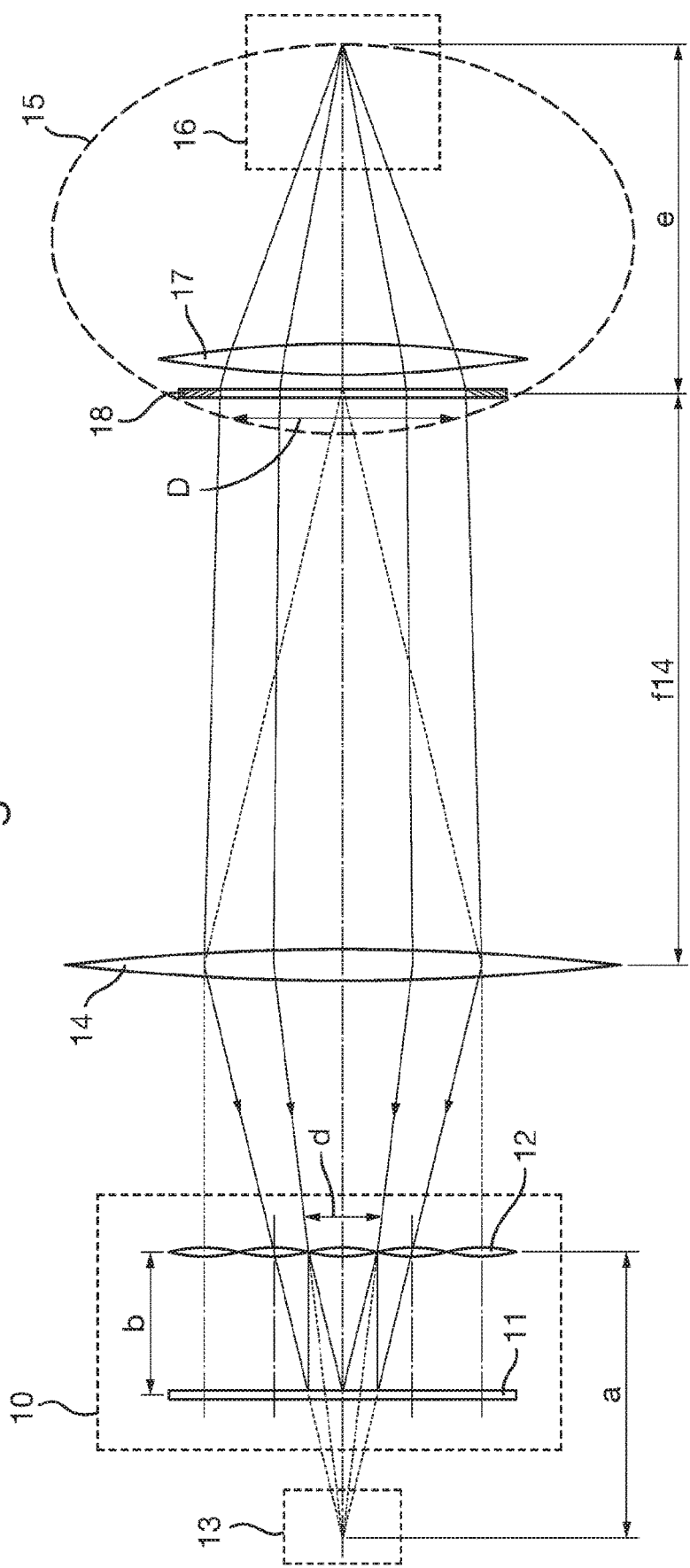
Figure 18:
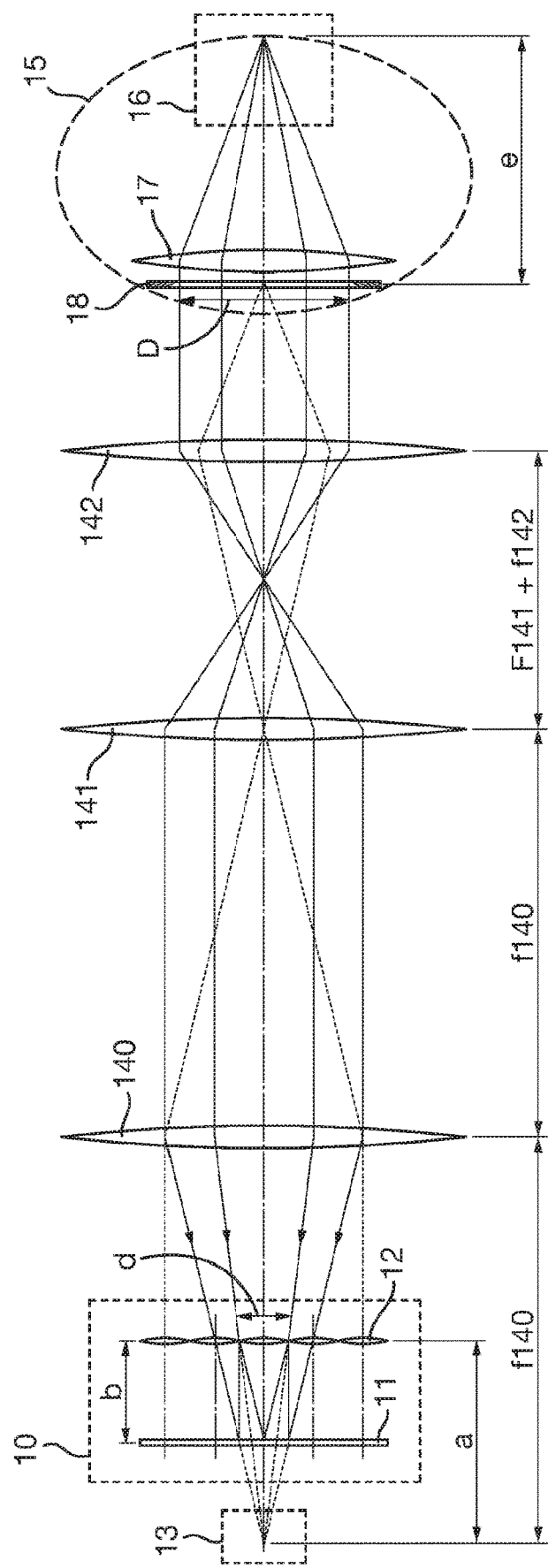

As shown in FIGS. 17 and 18, optionally, the first imaging subsystem comprises an objective lens group 14 and 140, respectively, configured to be positioned such that the eye pupil or an image of the eye pupil is at the back focal plane of the objective lens group. FIG. 17 is a schematic diagram illustrating an optical layout according to the invention. As shown in FIG. 17, optionally the eye pupil 18 is located in the back focal plane of the objective lens 14, where f14 represents the focal length of the objective lens group 14.

In this configuration equation 1 simplifies to $$\frac{b}{d} = \frac{4Re}{D^2} \times X, \text{ where } X \leq 82.$$

Preferably, this equation is satisfied with X≤50, X≤24, X≤20, X≤10, X≤5.0, or X≤2.0.

FIG. 18 is a schematic diagram illustrating an optical layout according to the invention. As shown in FIG. 18, optionally another two group of lenses 141, 142 are added between the eye to be imaged and the imaging lens group 140. An image of the eye pupil 18 is located in the back focal plane of the imaging lens group 140.

As shown in FIGS. 17 and 18, the eye pupil (FIG. 17) or an image conjugate of the eye pupil (FIG. 18) is located in the front focal plane of lens group 14 or 140 respectively. The exit pupil of the imaging system is located at infinity. With this configuration the f-number of the imaging lens is constant for the whole refocusing range. This insures that there is no cross talk between the lenslets of the lens array 12 of the sensor array 11.

Optionally, the ophthalmic imaging system is able to resolve details down to the diffraction limit imposed by the eye physical properties. Alternatively, the imaging resolution is limited for practical reasons such as the number of pixel of sensor array 11. For example, a sensor array 11 with 256 megapixels would be required to image a 30 degrees field of view down to the diffraction limit. Preferably, the resolution target for the ophthalmic imaging system is 60 lp/mm (line pair per millimeter).

Figure 12:
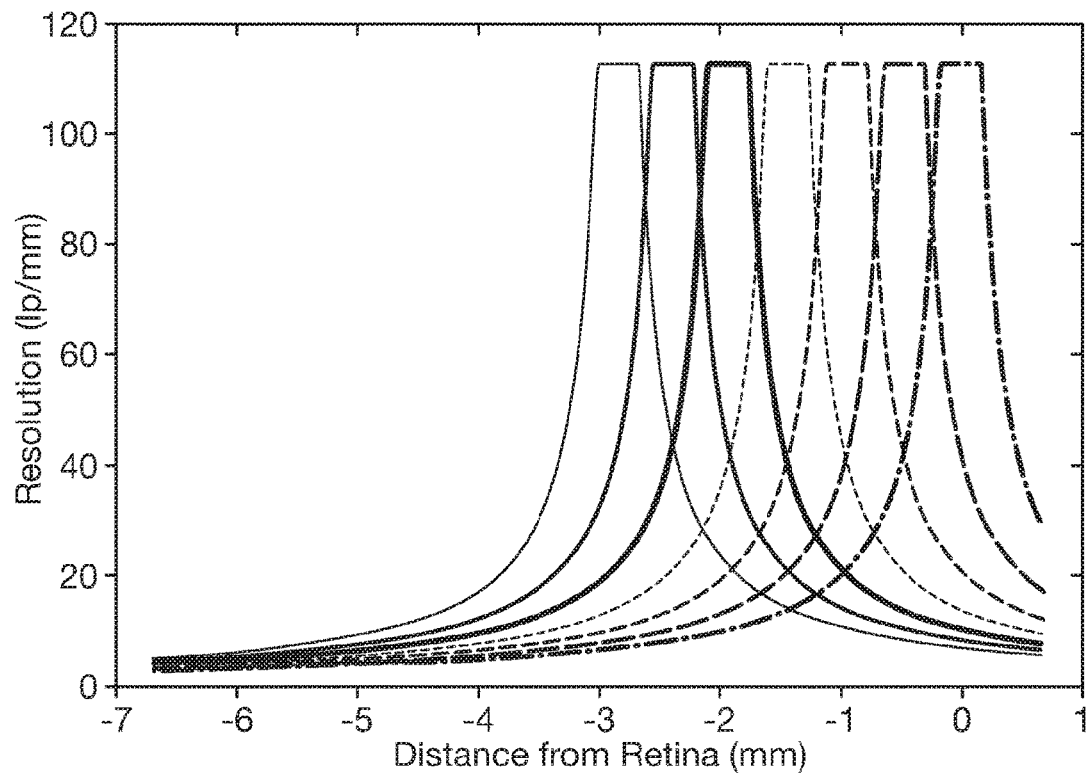
FIGS. 12 to 15 are graphs showing the relationship between distance from a reference plane and resolution according to the invention.
Figure 19:
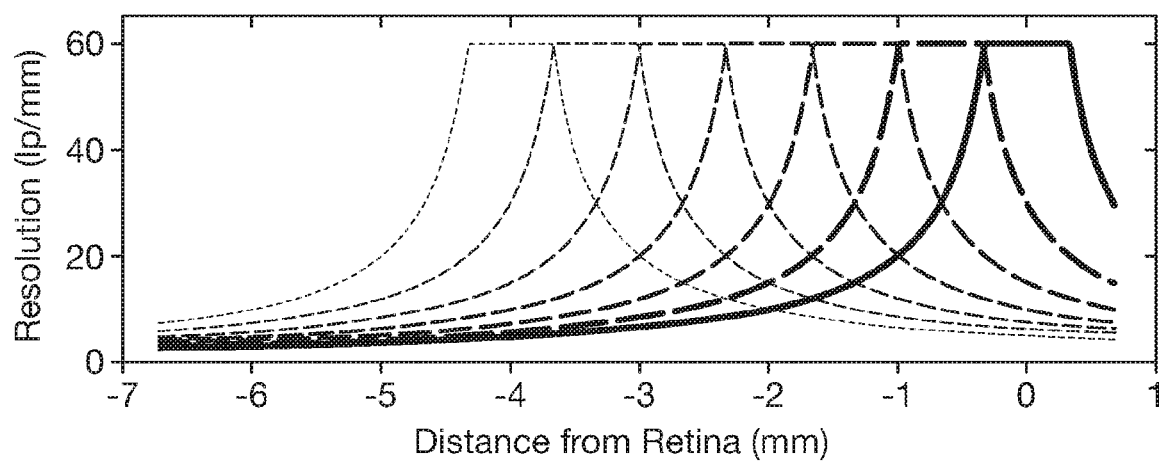
FIG. 19 is a graph showing the relationship between distance from a reference plane at a given target resolution according to the invention.

FIG. 12 is a graph showing the relationship between optical distance (of the refocusing plane) from the retina and image resolution. The theoretical resolution is represented by the horizontal line at a resolution of about 112 lp/mm. FIG. 19 is a graph showing the relationship between optical distance (of the refocusing plane) from the retina and image resolution, where the theoretical resolution is represented by the horizontal line at a resolution of about 60 lp/mm. The theoretical maximum resolution line is horizontal (rather than curved) because equation 1 is satisfied with X=1. In other words, the resolution is independent of the distance from the retina, i.e. the depth.

FIG. 12 shows seven resolution curves. Each resolution curve represents the image resolution provided by a different type of lens in the lens array 12. Each type of lens has a different focal length. As a result, the resolution peaks for the different types of lens are at different distances from the retina. Each peak is cut off (truncated) by the optimum resolution.

As shown in FIG. 12, the focal lengths for the different types of lens can be selected such that the optimum resolution is reached over a range of distances from the retina. Optionally, the focal lengths of the different lens types are chosen such that the depth-of-fields of the different types of lenses just touch in the graph of FIG. 12. It is not necessary that the depth-of-fields just touch. There may be some overlap. There may be some gap between the curves.

Optionally the ophthalmic imaging system 10 is diffraction-limited continuously over a depth range of planes to be imaged. As depicted in FIG. 12, for part of the range a first type of lens having a first optical power is diffraction-limited and for another part of the range a second type of lens having a second optical power is diffraction-limited. In other words, the resolution peaks of the different lenses overlap such that the ophthalmic imaging system 10 reaches the diffraction-limited resolution continuously over a range of distances from the retina.

As shown in FIG. 12, this can be achieved for seven different types of lens. The larger the number of different types of lenses, the greater the overall depth-of-field of the ophthalmic imaging system 10. However, a greater number of types of lenses means that the lenses of each particular type are distributed more sparsely across the lens array 12. As a result, the larger the number of different types of lenses, the larger the parameter v gets. This makes it more difficult to satisfy the requirement that parallax can be used. In other words, it is more difficult for every image point to be focused through at least two lenses of a particular type, when those lenses are spaced further apart. There can be a trade-off between depth-of-field and lateral imaging resolution.

Figure 15:
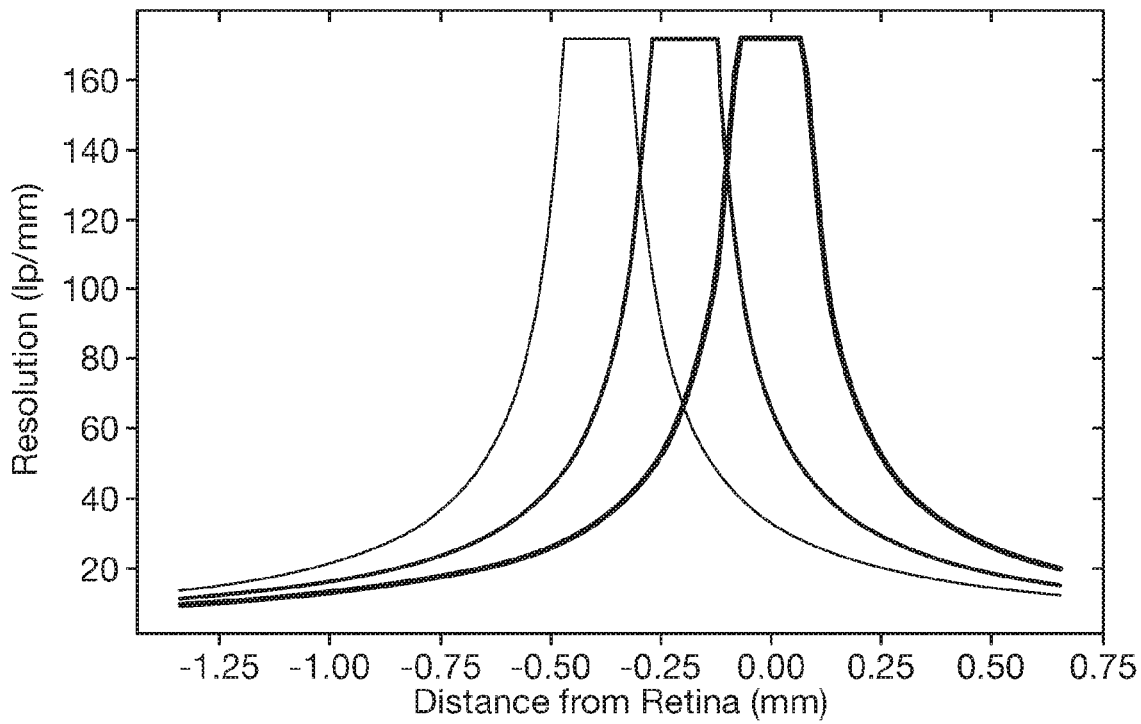

This is illustrated by a comparison between FIG. 12 and FIG. 15. The setup for FIG. 15 is similar to the setup for FIG. 12 in that equation 1 is satisfied with X=1. However, in the setup for FIG. 15, there are only three different types of lenses in the lens array 12. In FIG. 15, with a smaller number of types of lenses, the peak resolution (i.e. the diffraction limited resolution) is higher compared to in FIG. 12, with a larger number of types of lenses.

Figure 13:
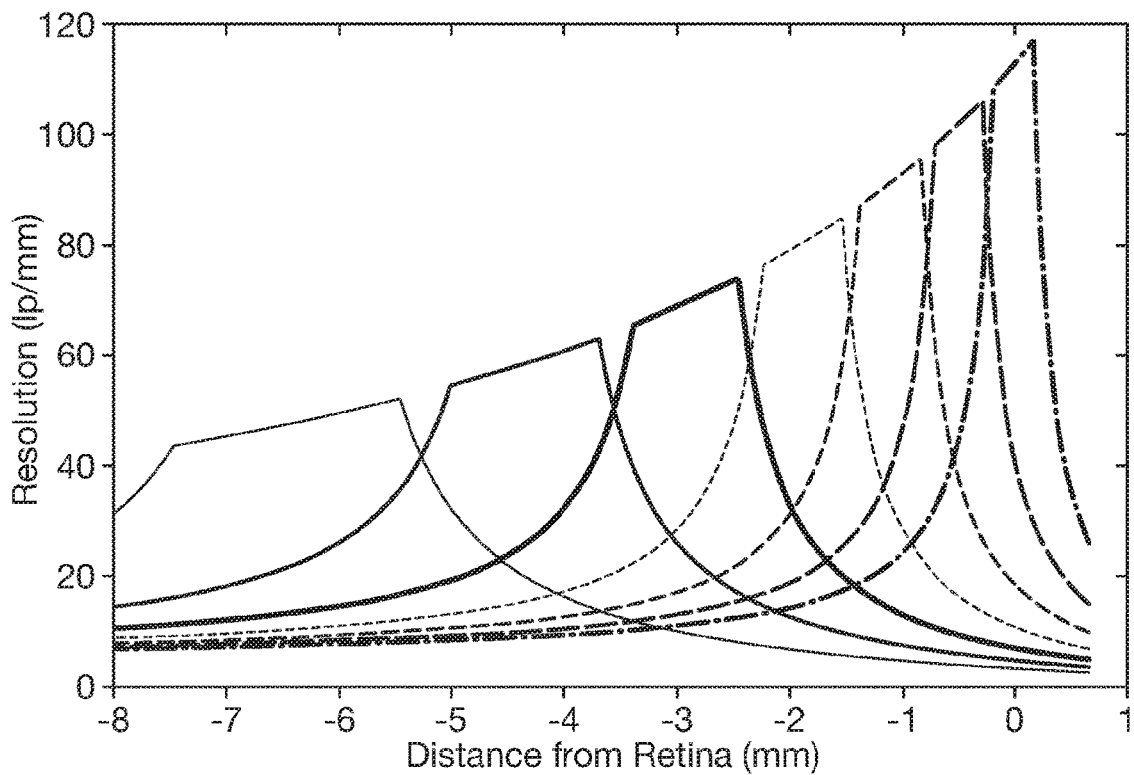

FIG. 13 is another graph similar to FIG. 12 but where equation 1 is satisfied with X≠1. In the graph of FIG. 13, X>1. FIG. 13 shows seven resolution curves corresponding to seven types of lens in the lens array 12. The resolution curves are cut off by the theoretical diffraction-limited resolution. The focal lengths of the different types of lens are selected so that different lenses reach the diffraction-limited resolution for different depths.

Comparing FIG. 13 to FIG. 12, it can be seen that the setup for FIG. 12 has the advantage that the image resolution is higher for distances up to about 3 mm from the retina. This is because equation 1 is satisfied with X closer to 1 (in fact for FIG. 12 X=1). However, the setup used for FIG. 13 has the advantage that for greater distances from the retina such as 4 mm and upwards from the retina, the image resolution is higher. This is because each image resolution curve for each type of lens is wider.

Comparing FIG. 12 to FIG. 13, there is shown a trade-off between high resolution at smaller distances from the retina and relatively high resolution at greater distances from the retina. The parameters for the ophthalmic imaging system 10 can be selected depending on the application.

For example, in the context of surgery, it may be desirable to image the surgical instruments. The surgical instruments may be positioned far from the retina such that the setup used for FIG. 13 may be more desirable. In contrast, for taking images very close to the retina, the setup used for FIG. 12 may be more desirable.

Figure 14:
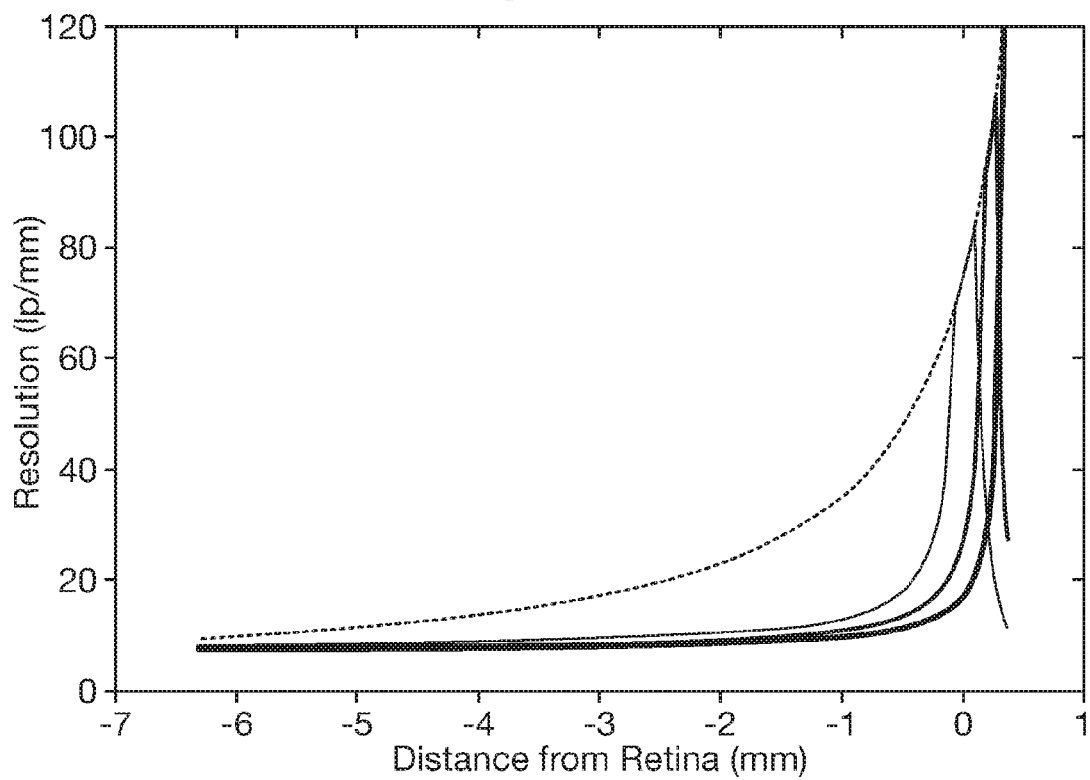

FIG. 14 shows a further graph showing the relationship between the distance from the retina and the image resolution. In the lens array 12 for the setup for FIG. 14, three different types of lens are used. Close to the retina, the resolution reaches a higher value compared to in either FIG. 12 or FIG. 13. However, the diffraction-limited resolution drops off very quickly away from the retina. This is because for the setup in FIG. 14, equation 1 is satisfied with a higher value of X (although X≤82 and so FIG. 14 represents an improvement relative to the prior art). For the setup shown in FIG. 14, the value of X is about 24.7.

Optionally, the lens array 12 is arranged such that X is variable (i.e. can be controlled). The lens array 12 is reconfigurable instead of fixed. For example, the lens array 12 may comprise an opto-electronic device such as spatial modulator. Alternatively, the lens array 12 may comprise micro optics with moving parts.

Optionally, equation 1 is satisfied with X<1. In this case the individual resolution curves for the different types of lenses get narrower (compared to FIG. 14), and the lateral resolution increases as the refocusing planes move away from the retina. When X<1, the diffraction limited resolution increases as the refocusing planes move away from the retina.

Figure 6:
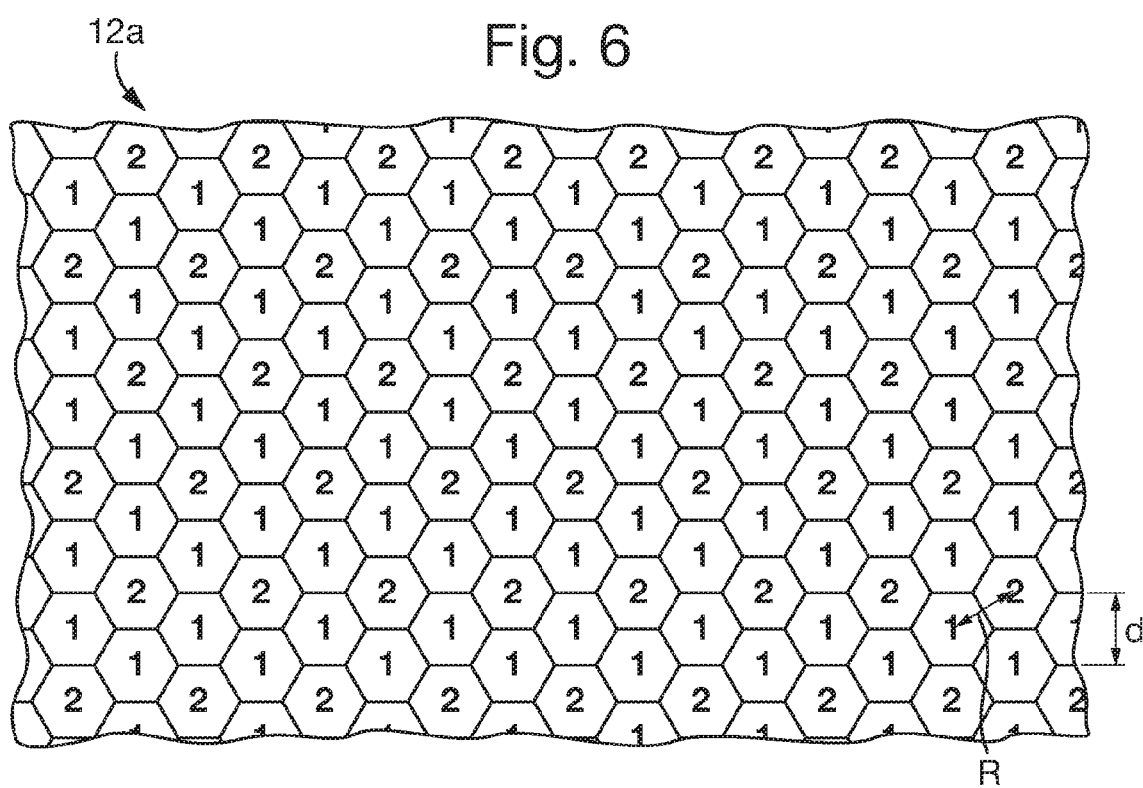
Figure 7:
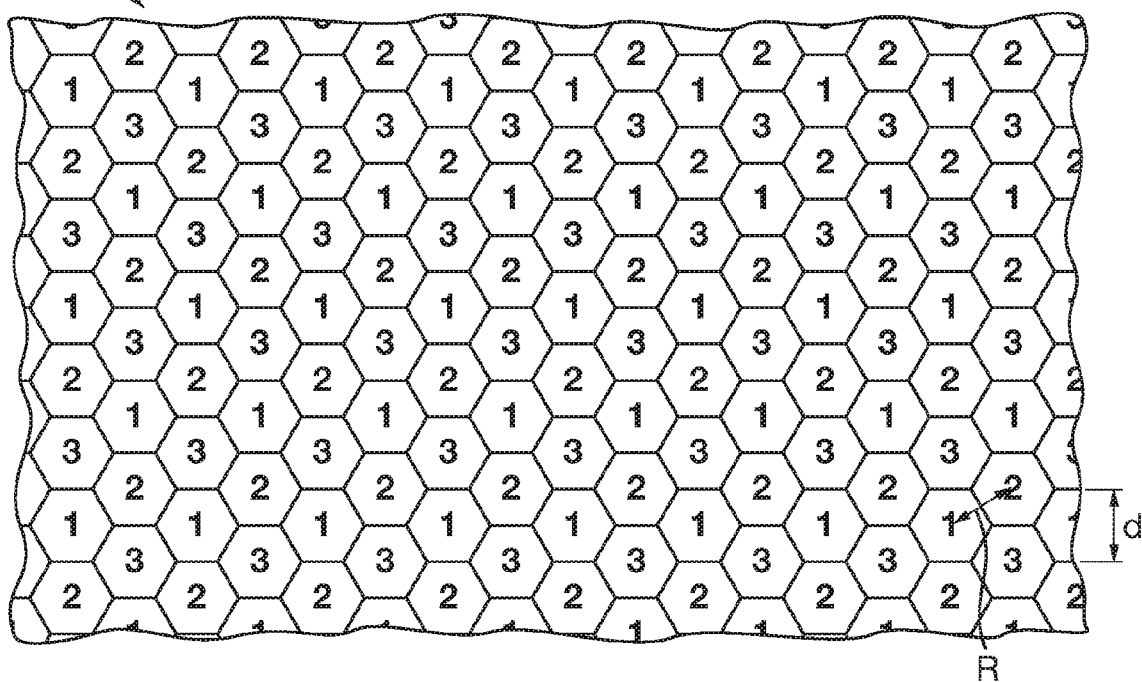
Figure 8:
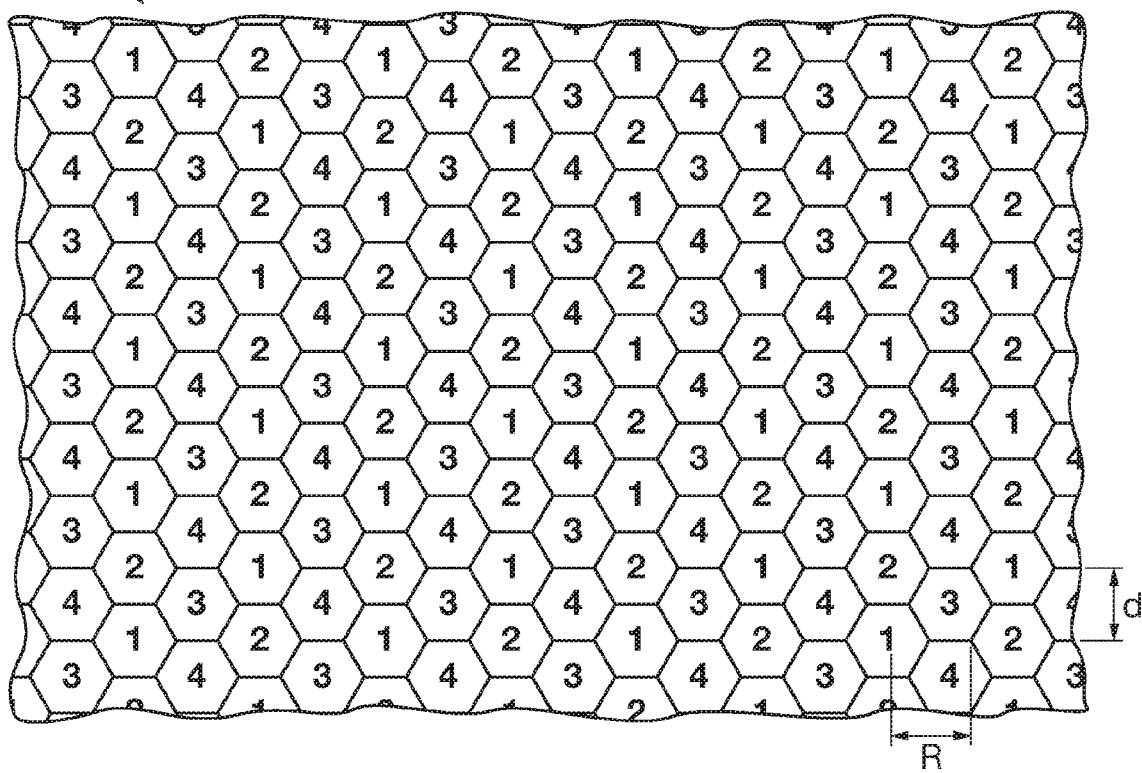
Figure 9:
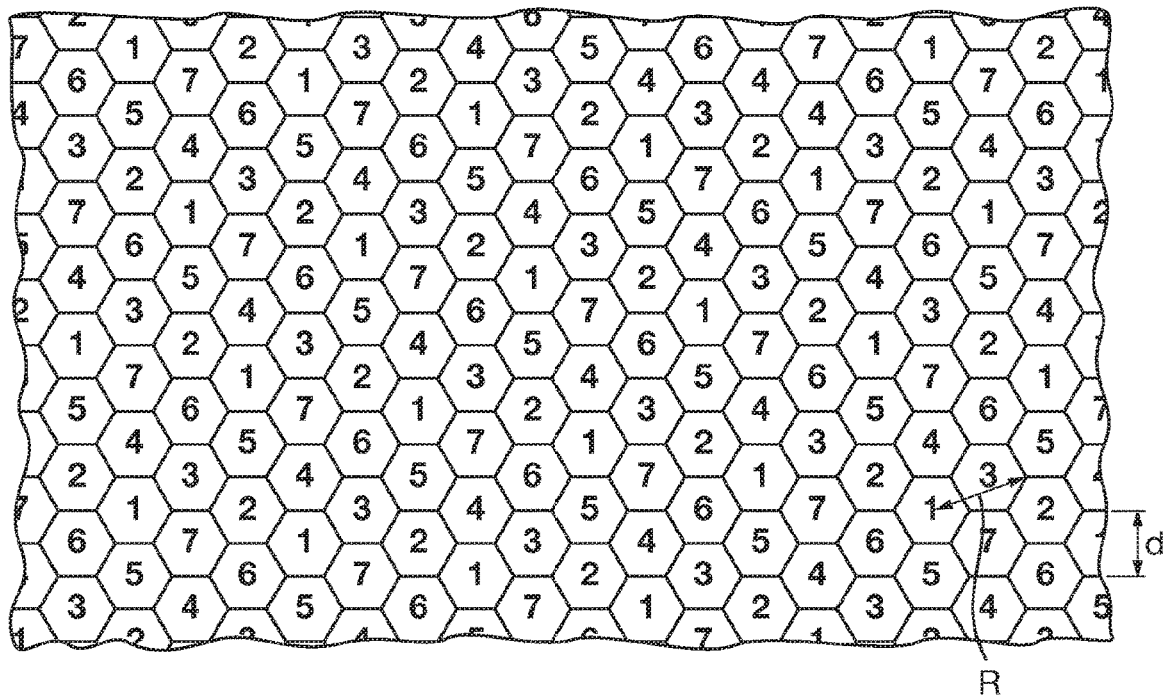

Optionally, the lens array 12 is composed of two types of lenslets. The lens array 12a is composed of two types of lenslets having different optical power. Optionally, each type of lens forms a regular grid, as shown in FIG. 6. In this configuration, v=4. This provides a longer depth-of-focus, i.e. a larger volume 16 can be image at high resolution. A plane near the retina is focused by the shaded lenslets of the lens array 12a on the sensor array 11, while a plane closer to the eye lens is focused by the unshaded lenslets of the lens array 12a. The number of types of lenslets is not particularly limited.

The two dimensional lens array 12 can be a regular tessellation of squares lenslets (v≈2.8) or a regular tessellation of hexagonal lens (v≈2.3). By way of example, a uniform two-types regular tessellation of hexagonal lenslets (v≈4); a uniform three-types tessellation of hexagonal lenslets (v≈4); a uniform four-types tessellation of hexagonal lenslets (v≈4.6); and a uniform seven-types tessellation of hexagonal lenslets (v≈6.1).

The two dimensional lens array 12 can also be a semi-regular tessellation of polygons. In that case, each type of lenslets have different dimensions or effective diameter. By way of example, a tessellation of octagonal and square lenslets (v≈2.8). This configuration has the same resolution power but with an extended depth-of-field. In another embodiment of the invention, a semi-regular tessellation of lenslets, comprising dodecagons, hexagons and squares (v≈2.9), and provides further depth-of-field without decreasing the lateral resolution.

Optionally, the ophthalmic imaging system 10 satisfies the equation $$\frac{b}{d} \leq 6.8.$$

The ratio $$\frac{b}{d}$$

is also called the effective f-number of the lenses of the lens array 12. By providing an upper limit of 6.8 for the effective f-number, lower aberrations compared to in the prior art are caused by the lenslets. Additionally, by providing that the effective f-number is less than or equal to 6.8, the overall size of the sensor array 11 can be reduced. Optionally.

$$\frac{b}{d} \leq 5.0,$$

and optionally $$\frac{b}{d} \leq 4.0.$$

Optionally, $$\frac{b}{d} \geq 1.0,$$

optionally $$\frac{b}{d} \geq 2.0,$$

and optionally $$\frac{b}{d} \geq 2.9.$$

By providing that the ratio is greater than or equal to 2.9, the imaging-lens cost can be reduced compared to known sensors that have lower effective f-numbers. Optionally, the effective f-number is 3.0.

Figure 10:
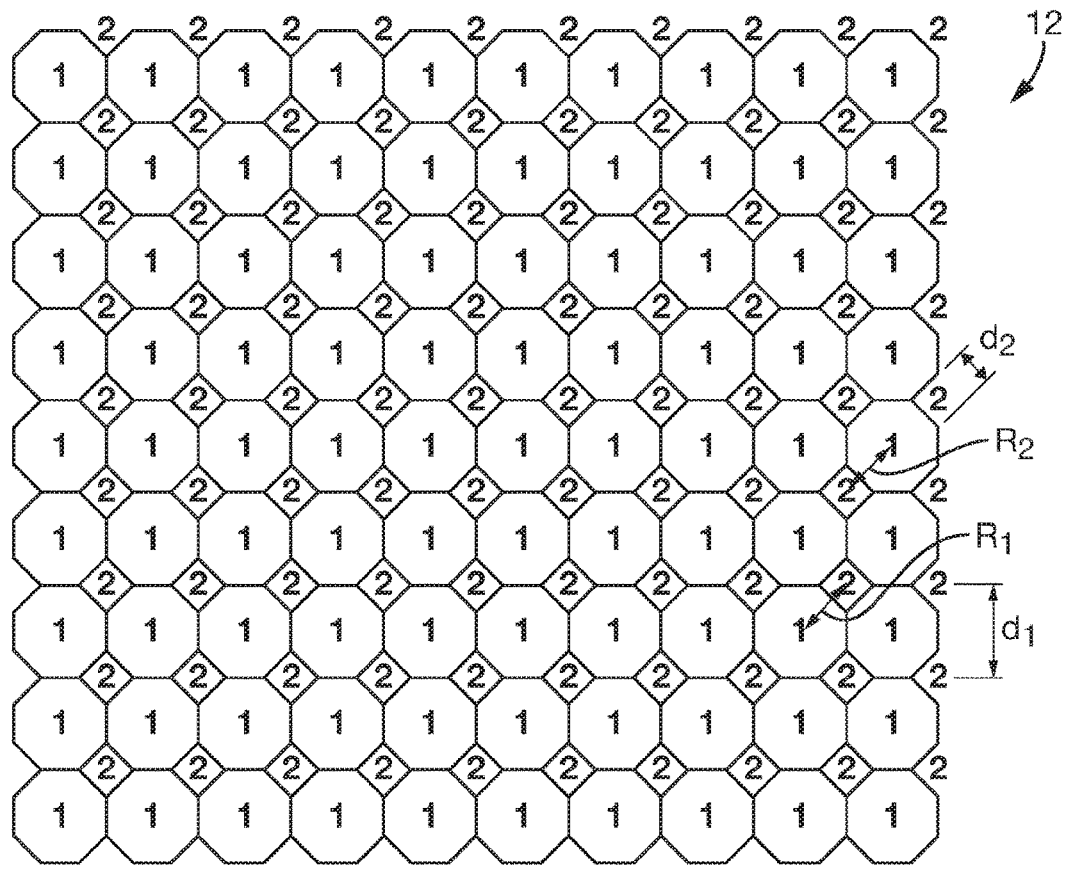
Figure 11:
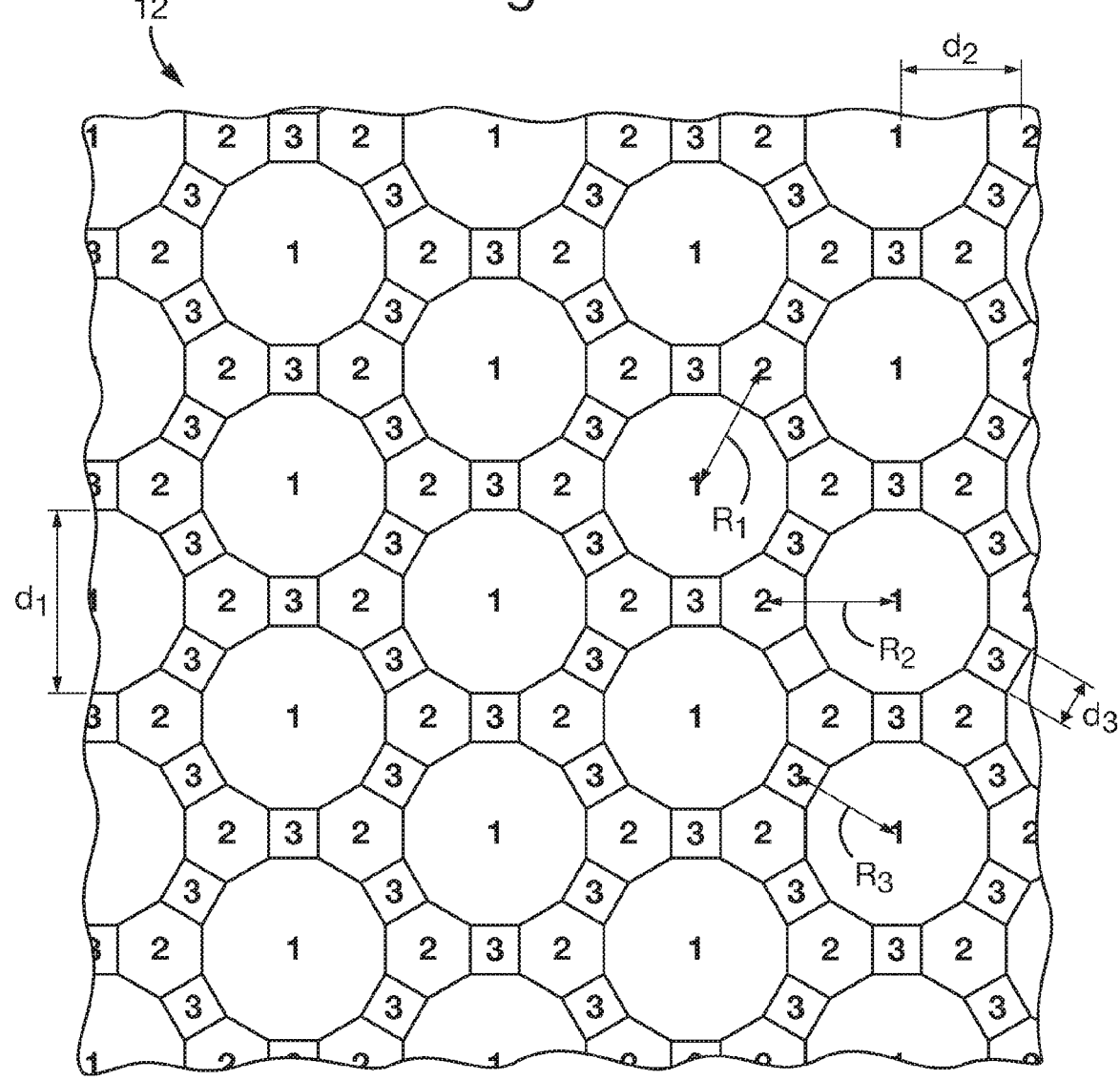

When the ophthalmic imaging system 10 comprises multiple types of lenses, the equations mentioned above are satisfied for each type of lens. Each type of lens may have different values for at least one of the parameters mentioned above. For example, FIG. 10 shows a configuration in which the two types of lenses have different diameters d, as indicated by the subscript numeral. However, the minimum radius R is the same for the two types of lenses. In the configuration shown in FIG. 11, the three types of lenses have different diameters d. The minimum radius R is the same for two of the three types of lenses, and different for type 3.

In the discussion above, all distances are optical distances (unless otherwise explicitly stated), rather than physical distances. For example, a distance e of 17 mm may correspond to a physical distance of about 23 mm but through a medium that has a refractive index of about 1.3, so that optical distance is about 17 mm.

Optionally, the optical distance e is 17 mm and the pupil diameter D is 7 mm. However, other values for e and D can be used, for example if the ophthalmic imaging system 10 is for imaging differently shaped eyes. Optionally, the optical distance e≥5.0 mm, optionally e≥10 mm, and optionally e≥15 mm. Optionally, the optical distance e≤100 mm, optionally e≤50 mm, and optionally e≤20 mm. Optionally, the diameter D≥1.0 mm, optionally D≥2.0 mm, and optionally D≥5.0 mm. Optionally, the diameter D≤50 mm, optionally D≤20 mm, and optionally D≤10 mm.

Optionally, the lenslets of the lens array 12 are achromatic. Optionally, the lenslets of the lens array 12 are composed of two or more materials. Optionally, the surfaces of the lenslets of the lens array 12 are aspheric. For example, this can be achieved using plastic optics. Optionally, the lens array 12 is machined, for example using diamond machining. This helps to improve surface accuracy. Alternatively, a mold can be machined and the lens array 12 can be produced by injection molding. Alternatively, the lens array 12 can be produced using polymer on a glass wafer with multiple layer of polymers (for example as described in more detail in Dannberg, Peter, Frank Wippermann, Andreas Brückner, Andre Matthes, Peter Schreiber, and Andreas Bräuer. "Wafer-Level Hybrid Integration of Complex Micro-Optical Modules." Micromachines 5, no. 2 (Jun. 5, 2014): 325-40).

Optionally, the invention can be used to image an eye so as to diagnose a medical condition.

According to the present invention, equation 1 with X=1 defines a condition for which the spatial resolution of the ophthalmic imaging system 10 remains constant for all digital refocusing distances or two-dimensional planes within volume 16. While this condition constitutes a preference, departures from this condition remain within the scope of the invention. It will be appreciated by those skilled in the art that by departing from this condition, the imaging depth can be extended but with a loss of lateral imaging resolution.

The invention preferably images the interior of the eye through the whole dilated pupil. It offers better depth discrimination.

The figures and previous description relate to preferred features by way of illustration only. It should be noted that from the following discussion, alternative features of the structures and methods disclosed herein will be readily recognized as viable alternatives. The equipment described above is by way of example only, and it will be appreciated that it may be modified in several different ways while remaining within the scope of the present invention.

In particular, negative power micro-lenses or a Galilean vs Keppler telescopic arrangement can be used for the micro-lenses. Micro-lenses with several refractive surfaces and thicknesses can be used.

We claim:

1. An ophthalmic imaging system comprising:
   a first imaging subsystem configured to form a primary image of the interior of an eye through the diameter of the eye pupil;
   a sensor array; and
   a second imaging subsystem comprising a lens array configured to form an array of secondary images on the sensor array;
   wherein the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centred on the centres of the lenses (R) obey the relation $$\frac{b}{d} = \frac{Xe}{D}\left(\frac{1}{\frac{D}{4R} - 1}\right), \text{ where } X \leq 82.$$

2. The system as recited in claim 1, wherein X≤24.
3. The system as recited in claim 1, wherein X≤5.0.
4. The system as recited in claim 1, wherein X≥0.50.
5. The system as recited in claim 1, wherein the lens array is arranged such that X is variable.
6. The system as recited in claim 1, wherein D=7 mm and e=17 mm.
7. The system as recited in claim 1, wherein for each type of lens of the lens array, the optical distance between the lenses and the sensor array (b) and the diameter of the lenses (d) obey the relation $$\frac{b}{d} \leq 6.8.$$

8. The system as recited in claim 1, wherein for each type of lens of the lens array, the optical distance between the lenses and the sensor array (b) and the diameter of the lenses (d) obey the relation $$\frac{b}{d} \geq 2.9.$$

9. The system as recited in claim 1, wherein the first imaging subsystem comprises an objective lens group, a first intermediate lens group and a second intermediate lens group, wherein in use the first intermediate lens group and the second intermediate lens group are configured to be positioned optically between the objective lens group and the eye pupil.

10. The system as recited in claim 9, wherein the first intermediate lens group and the second intermediate lens group are configured to relay an image of the eye pupil onto the principal plane of the objective lens group.

11. The system as recited in claim 10, wherein the first intermediate lens group and the second intermediate lens group are configured to magnify the image of the eye pupil by a ratio f141/f142 where f141 is the focal length of the first intermediate lens group and f142 is the focal length of the second intermediate lens group.

12. The system as recited in claim 11, wherein for each type of lens of the lens array, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centred on the centres of the lenses (R) obey the relation $$\frac{b}{d} = \frac{Xe}{D}\left(\frac{1}{\frac{D}{4R} - \frac{f142}{f141}}\right), \text{ where } X \leq 82.$$

13. The system as recited in claim 1, wherein the first imaging subsystem comprises an objective lens group configured to be positioned such that the eye pupil or an image of the eye pupil is at the back focal plane of the objective lens group.

14. The system as recited in claim 13, wherein for each type of lens of the lens array, the optical distance between the lenses and the sensor array (b), the diameter of the lenses (d), the diameter of the eye pupil (D), the optical distance between the object plane to be imaged and the eye lens (e) and the minimum radius of circle required to cover the lens array with circles having the minimum radius if the circles were centred on the centres of the lenses (R) obey the relation $$\frac{b}{d} = \frac{4XRe}{D^2}, \text{ where } X \leq 82.$$

15. The system as recited in claim 1, wherein the first imaging subsystem is a variable power imaging subsystem.

16. A vitreoretinal surgical imaging system comprising the system as recited in claim 1.

* * * * *